(12) United States Patent
Odell et al.

(10) Patent No.: US 6,951,128 B2
(45) Date of Patent: Oct. 4, 2005

(54) POLYMERIC SOLUTIONS RHEOMETER

(75) Inventors: Jeffrey Arthur Odell, Bristol (GB); Stephen Paul Carrington, Bristol (GB)

(73) Assignee: University of Bristol, (GB)

( * ) Notice: Subject to any disclaimer, the term of this patent is extended or adjusted under 35 U.S.C. 154(b) by 32 days.

(21) Appl. No.: 10/433,810
(22) PCT Filed: Dec. 7, 2001
(86) PCT No.: PCT/GB01/05427

§ 371 (c)(1),
(2), (4) Date: Nov. 25, 2003

(87) PCT Pub. No.: WO02/46720

PCT Pub. Date: Jun. 13, 2002

(65) Prior Publication Data
US 2004/0074287 A1 Apr. 22, 2004

(30) Foreign Application Priority Data

Dec. 7, 2000 (GB) .................................. 0029873
Sep. 12, 2001 (GB) .................................. 0122056

(51) Int. Cl.[7] .......................................... G01N 11/10
(52) U.S. Cl. .................................................. 73/54.41
(58) Field of Search ............................ 73/54.41, 54.24, 73/54.25, 54.26, 54.27, 579, 590, 596, 601

(56) References Cited

U.S. PATENT DOCUMENTS

| 4,735,097 | A | * | 4/1988 | Lynnworth | 73/861.28 |
|---|---|---|---|---|---|
| 5,056,357 | A | * | 10/1991 | Dymling et al. | 73/54.41 |
| 5,357,784 | A | | 10/1994 | Collier | 73/54.14 |
| 5,365,778 | A | * | 11/1994 | Sheen et al. | 73/54.41 |
| 5,433,112 | A | * | 7/1995 | Piche et al. | 73/597 |
| 5,456,105 | A | | 10/1995 | James | 73/54.01 |
| 5,646,039 | A | * | 7/1997 | Northrup et al. | 435/287.2 |
| 6,378,357 | B1 | * | 4/2002 | Han et al. | 73/54.41 |
| 6,446,494 | B2 | * | 9/2002 | Hastings et al. | 73/54.41 |

FOREIGN PATENT DOCUMENTS

| DE | 107 980 | 3/1973 |
|---|---|---|
| EP | 0 899 556 | 3/1999 |

OTHER PUBLICATIONS

Kapoor et al. "Dynamic and Extensional Properties of Starch in Aqueous Dimethylsulfoxide" *Carbohydrate Polymers* 2000, 42, 323-335.

* cited by examiner

*Primary Examiner*—Charles Garber
(74) *Attorney, Agent, or Firm*—Ohlandt, Greeley, Ruggiero & Perle, L.L.P.

(57) ABSTRACT

A method for determination of the extensional rheological properties of a liquid comprises application to a sample of liquid in a closed system of a pulsed oscillatory alternating flow in a geometry creating an extension flow surrounding a stagnation point and measuring the pressure drop in the liquid across the stagnation point. The alternating displacement may be applied from the ends of each limb in a given direction simultaneously, thereby providing symmetrical flow. The method may be carried out on very small sample volumes of dilute polymer solutions.

11 Claims, 1 Drawing Sheet

POLYMERIC SOLUTIONS RHEOMETER

FIELD OF THE INVENTION

This invention relates to the rheology of dilute polymeric solutions and in particular provides apparatus and a method for measurement of the rheological properties of such solutions under non-shear, especially extensional, flow conditions. The invention also enables the molecular weight distribution of polymers, especially the high tails thereof, to be assessed.

DISCUSSION OF THE BACKGROUND ART

It is possible to measure the shear properties of polymeric liquids using conventional apparatus such as a cone and plate rotational rheometer but such measurements are of little relevance to behaviour under other flow conditions, especially extensional flow conditions which have the ability significantly to "stretch" macromolecules, providing orders of magnitude increases in elastic forces and extensional viscosity. Indeed, especially with dilute solutions of high molecular weight linear polymers, different flows can produce dramatically different rheological properties, in that such solutions may exhibit a reduction in viscosity under shear conditions but an increase under extensional flow conditions, under which the polymer macromolecules tend to become stretched out. Thus, a measurement of the rheological properties of such solutions under shear conditions is unlikely to provide an adequate indication of rheological performance under real flow conditions.

In order to achieve full chain extension of a polymer molecule so that the rheological properties of solutions thereof can be measured under extensional flow conditions, it is necessary for the flow field to provide an adequate stretching force and to maintain the force for a sufficient time. Generally, the strain in a given fluid element should be at least 100×, especially if the polymer molecules are long and highly flexible. In order to meet these criteria, it has hitherto been necessary to use a continuous pumping system applied to a minimum sample volume of about 200 ml, although typically a 500 ml sample has been used. However, for biological systems such sample volumes may not be obtainable and for polymer systems such volumes may be prohibitively expensive and the large amounts of organic solvents required for such sample volumes may represent a hazard.

SUMMARY OF THE INVENTION

It is an object of the present invention to provide apparatus and a method for determining the rheological properties of liquids, especially of dilute polymeric solutions, under non-shear and especially extensional flow conditions, in which the sample volume is small.

It is another object of the invention to provide a method of measuring the molecular weight distribution of polymers, especially of polymers such as polyolefins which are not normally soluble at room temperature and which are difficult to assess by means such as gel permeation chromatography. The existence of high tails in the molecular weight distribution of polyethylene, polypropylene and other such polymers is very influential in the processing and properties thereof and a way of evaluating the molecular weight distribution is therefore required.

According to one aspect of the invention, a method for determination of the extensional rheological properties of a liquid comprises application to a sample of liquid in a closed system a pulsed oscillatory alternating flow in a geometry which will create an extensional flow surrounding a stagnation point and measuring the pressure drop in the liquid across the stagnation point.

The method of the invention may be used in conjunction with optical retardation measurements to assess molecular properties of dissolved macromolecules, in particular the molecular weight distribution and especially the high molecular weight tail thereof.

According to another aspect of the invention, apparatus for determination of the rheological properties of a liquid comprises a sample chamber including at least four intersecting limbs disposed in two mutually orthogonal directions, means to apply an alternating pulsed displacement in each direction and means to measure the pressure drop as between the directions.

The alternating pulsed displacement, achieved by application of a pulsed pressure force to the sample liquid in opposing pairs of limbs, produces a stagnation point at the intersection zone which provides a site of infinite residence time to allow stretching of solute macromolecules to take place. Thus, once a steady state has been achieved in terms of the pressure drop measurements, optimum stretching of the polymer molecules will have occurred. The alternating displacement may be applied from the ends of each limb in a given direction simultaneously, to provide symmetrical flow. Asymmetric flow may be provided by applying displacement from the end of only one limb in each direction, or by applying different displacements from the ends of each limb in a given direction, either in phase or out of phase.

The method can be carried out in sample volumes of around 1 ml or even less, the sample chamber being closed and therefore presenting a clean and environmentally-isolated system for testing samples comprising biological or hazardous materials. Alternatively and in order to reduce the sample volume further, test fluid may be injected directly into the stagnation point zone, the remainder of the apparatus containing immiscible fluid. This would reduce test volumes to as little as 50 $\mu$l.

Where, for example, the liquid is a solution of a high molecular weight polymer in a low viscosity solvent, the pressure drop measurement for pure solvent can also be measured and subtracted from the figure for the solution, the resultant figure can be divided by the strain rate to yield a figure representing the effective extensional viscosity, including a contribution from the shear viscosity.

The shear viscosity can be determined by application of the inventive method by flow or pulsed displacement in a single pair of limbs, thereby avoiding creation of a stagnation point. The contribution of shear viscosity can then be subtracted from the result using a stagnation point to give a result for pure extensional flow.

The displacement may be applied by pressure-application means comprising pumps driven by piezo-electric crystals although other means such as stepper motors may be employed, including magnetostrictive, linear actuators, solenoid actuators, piezo inch-worm and hydraulic actuators. Such pumps can conveniently be computer-controlled according to computer-synthesized waveforms providing the ability to apply a repetitive or a discrete flow profile, as required. Sinusoidal, square, ramped square, saw-tooth and exponential waveforms may be employed. Exponential waveforms are especially useful in molecular weight determination. The pumping pressure is preferably applied from each end of each limb and the pumping rates can be controlled separately to provide asymmetric flows or in order to avoid creation of a stagnation point, as already described with reference to determination of shear viscosity only. Pressure drop can be measured by pressure transducers disposed in the limbs of the apparatus.

The stretching of dissolved molecules at the stagnation point may be monitored by birefringence studies, that is, strain induced optical retardation. This may be achieved or enhanced by the use of modulated solid-state lasers, fast-cooled CCD (Charged Coupled Device) detectors and phase-sensitive detection techniques.

The use of the invention results in very little turbulence in the liquid sample, since actual dynamic flow is minimized, and in any event perturbation can be reduced by controlling the molecular strain, thus enabling investigation of semi-dilute solutions. The molecular weight distribution or other properties of dissolved macromolecules may also be assessed, especially where the polymers are not normally soluble at room temperature, since the apparatus together with its small-volume, enclosed sample of liquid can readily be heated to temperatures at which dissolution will occur. This cannot be done with conventional larger-volume continuous pumping systems.

The applied displacement can be controlled to vary the ramp rate, waveform and frequency in order to model, for example, porous media flows in tertiary oil recovery. Asymmetric displacement application, for example by controlling the piezo-electric crystals, can enable other flows, for example Poisseiulle, or capillary entrance, to be investigated, or simple shear to be optionally combined with extensional components. An alternative mode of operation is under controlled pressure, using feedback control between the pressure transducers and the piezo-electric or other drive pumps.

Furthermore, the molecular weight of polymer fragments which are formed by scission of dissolved macromolecules at or across the stagnation point can be determined, together with their effect on the rheology of the solution.

Other applications include investigating the behaviour of biologically functional molecules such as mucin and synovial fluid and the role of flow in diseases such as cystic fibrosis and osteo-arthritis with the capability to perform experiments at in vivo temperatures; further investigation of polymer physics with a view to resolving outstanding issues such as hysteresis in the stretching and relaxation of molecules; and the investigation of thermo-mechanical degradation of, especially, high molecular weight polymers or high molecular weight drugs in novel inoculation techniques.

BRIEF DESCRIPTION OF THE DRAWINGS

Embodiments of the invention will now be described by way of example with reference to the accompanying drawings, of which

DETAILED DESCRIPTION OF THE PREFERRED EMBODIMENT

Figure 1:
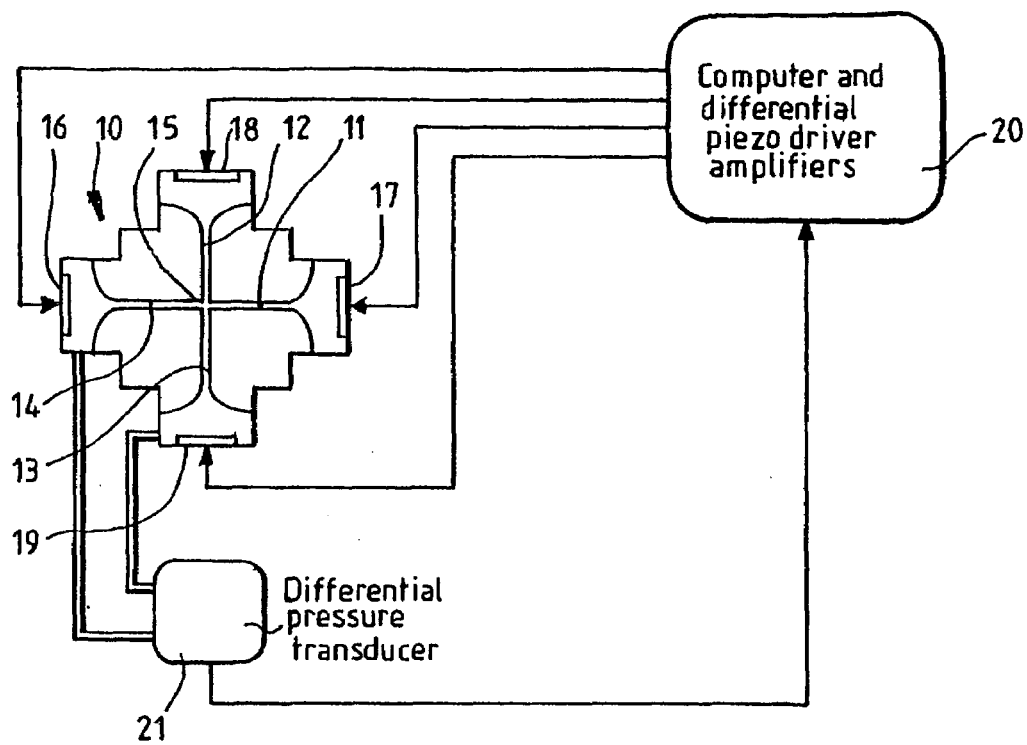
FIG. 1 is a schematic view of a rheometer and pressure circuit and FIG. 2 is a schematic view of a rheometer with optical retardation detection.

With reference to FIG. 1, the rheometer shown generally as 10 has a chamber comprising four limbs 11, 12, 13, 14 in two orthogonal directions, the limbs intersecting at 15. Each end of each limb has a piezoelectric driving crystal 16, 17, 18 19; the crystals are connected to computer-controlled differential piezo driver amplifiers 20 so that the crystals at each end of limbs in a given direction, say 16 and 17, operate in synchronism to cause the liquid to flow from limbs 11 and 14 through the intersection 15 to the limbs 12 and 13.

The crystals 18, 19 are then operated to pressurize the liquid in limbs 12 and 13 through the intersection to limbs 11 and 14 and the alternating process is repeated rapidly such that a stagnation point is created at the intersection 15, where there is a net zero flow of liquid such that molecular stretching will occur, even for extremely small volume displacements in the chamber as a whole.

Pressure drop as between the two limbs is measured by a differential pressure transducer 21 the output of which is applied to the computer which also controls the piezo driver amplifiers 20.

Figure 2:
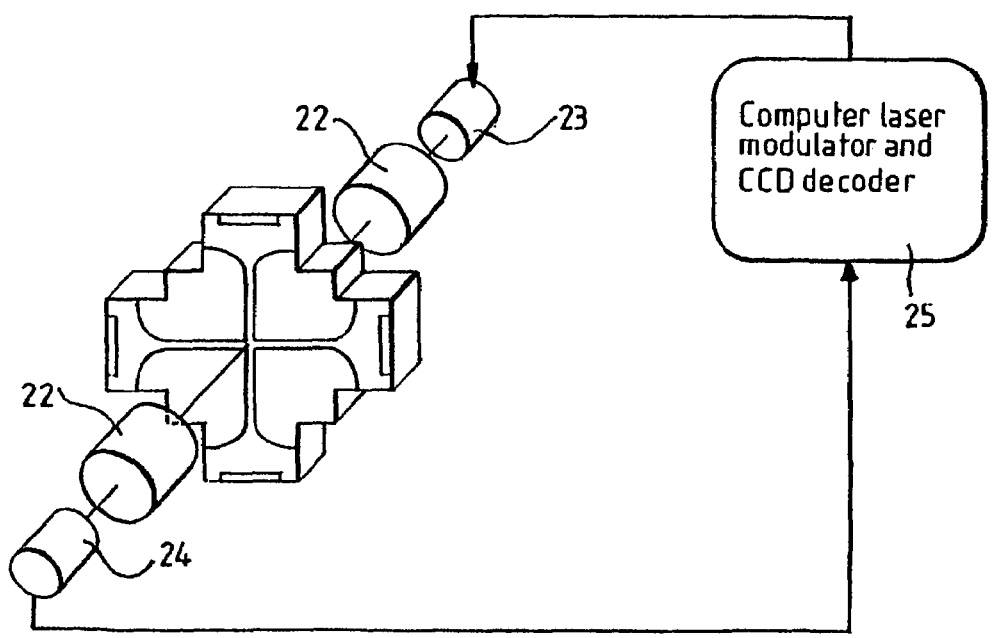

Referring to FIG. 2, the stretching of molecules at the stagnation point is assessed through birefringence between crossed polars 22, measured by means of a CCD detector 24 and solid state laser 23 connected to a computer laser modulator and CCD decoder 25.

In one embodiment the apparatus utilises linear actuator stepper motor drives and a flow cell with 700 $\mu$m wide and 1.6 mm deep limbs. This apparatus has been shown to be capable of achieving stable oscillatory extensional flow fields under computer control. Extensional strain rates up to $1500s^{-1}$ have been achieved, corresponding to the stretching of $3.5 \times 10^6$ molecular weight atactic polystyrene (aPS) in dioctyl phthalate (DOP). After subtraction of the shear component, extensional viscosities have been measured for aPS/DOP solutions of 100 ppm (0.01%) concentration. Birefringent signals have been detected which allow the molecular weight distribution to be determined from aPS/DOP solutions of 10 ppm (0.00%) concentration.

Alternative fabrication techniques can produce cell limbs as narrow as 50 $\mu$m width. At the same time, the piezoelectric crystals increase the available displacement rate. This development of the apparatus will yield strain rates from 0 to $1 \times 10^5 s^{-1}$ in a stable laminar flow regime. This will enable the stretching and detection of macromolecules above $1 \times 10^5$ molecular weight a PS equivalent.

What is claimed is:

1. A method for determination of the extensional rheological properties of a liquid, the method comprising applying to a sample of liquid in a closed system of a pulsed oscillatory alternating displacement flow in a geometry creating an extensional flow surrounding a stagnation point and measuring the pressure drop in the liquid across the stagnation point.

2. A method according to claim 1, in which the alternating displacement is applied from the ends of each limb in a given direction simultaneously, thereby providing symmetrical flow.

3. A method according to claim 1, in which the flow is asymmetric.

4. A method according to claim 3, in which the displacement is applied from the end of only one limb in each direction.

5. A method according to claim 3, in which different displacements are applied from the ends of each limb in a given direction either in phase or out of phase.

6. A method according to claim 1, in which the sample

7. A method according to claim 1, in which test fluid is injected directly into the stagnation point, the remainder of the apparatus containing immiscible fluid.

8. A method according to claim 1, in which the liquid is a solution of a high molecular weight polymer in a low viscosity solvent, the method including measuring the pressure drop for pure solvent subtracting the figure thus determined from the figure for the solution and dividing the resultant figure by the strain rate to yield a figure representing the effective extensional viscosity, including a contribution from the shear viscosity.

9. A method according to claim 1, in which the displacement is applied by pressure-application means comprising pumps driven by piezo-electric crystals.

10. A method according to claim 9, in which the pumps are computer-controlled according to computer-synthesized waveforms to provide the ability to apply a repetitive or a discrete flow profile.

11. Apparatus for determination of the rheological properties of a liquid, comprising:
- a sample chamber including at least four intersecting limbs dispersed in two mutually orthogonal directions;
- means for applying alternating pulsed displacement in each of said mutually orthogonal directions; and
- means for measuring the pressure drop between said directions;
- whereby said means for applying alternating pulsed displacement results in a stagnation point at the intersection zone of the opposing pairs of limbs.

* * * * *